(12) United States Patent
Yokhin et al.

(10) Patent No.: US 7,120,228 B2
(45) Date of Patent: Oct. 10, 2006

(54) COMBINED X-RAY REFLECTOMETER AND DIFFRACTOMETER

(75) Inventors: Boris Yokhin, Nazareth Illit (IL); Isaac Mazor, Haifa (IL); Tzachi Rafaeli, Givat Shimshit (IL)

(73) Assignee: Jordan Valley Applied Radiation Ltd., Migdal Ha'emek (IL)

( * ) Notice: Subject to any disclaimer, the term of this patent is extended or adjusted under 35 U.S.C. 154(b) by 50 days.

(21) Appl. No.: 10/946,426

(22) Filed: Sep. 21, 2004

(65) Prior Publication Data
US 2006/0062350 A1    Mar. 23, 2006

(51) Int. Cl.
*G01B 15/02* (2006.01)

(52) U.S. Cl. .............................. 378/90; 378/70; 378/76; 378/89

(58) Field of Classification Search .................. 378/76, 378/84, 88, 89, 90, 46, 70; 250/559.11
See application file for complete search history.

(56) References Cited

U.S. PATENT DOCUMENTS

| | | | |
|---|---|---|---|
| 4,446,568 A * | 5/1984 | Williams et al. ................ | 378/3 |
| 4,725,963 A | 2/1988 | Taylor et al. | |
| 4,989,226 A | 1/1991 | Woodbury et al. | |
| 5,151,588 A | 9/1992 | Kiri et al. | |
| 5,574,284 A | 11/1996 | Farr | |
| 5,619,548 A | 4/1997 | Koppel | |
| 5,740,226 A | 4/1998 | Koppel | |
| 5,923,720 A * | 7/1999 | Barton et al. ................. | 378/84 |
| 5,949,847 A | 9/1999 | Terada et al. | |
| 5,963,329 A | 10/1999 | Conrad et al. | |
| 6,041,098 A | 3/2000 | Touryanski et al. | |
| 6,192,103 B1 | 2/2001 | Wormington et al. | |
| 6,226,347 B1 | 5/2001 | Golenhofen | |
| 6,226,349 B1 | 5/2001 | Schuster et al. | |
| 6,381,303 B1 | 4/2002 | Vu et al. | |
| 6,389,102 B1 | 5/2002 | Mazor et al. | |
| 6,453,006 B1 | 9/2002 | Koppel et al. | |

(Continued)

FOREIGN PATENT DOCUMENTS

JP    9-308339    12/1997

OTHER PUBLICATIONS

Neissendorfer, et al., The energy-dispersive reflectometer/diffractometer at BESSY-I, 1999, IOP Publishing, Ltd., Measurement Science Technology, vol. 10, pp. 354-361.*

(Continued)

*Primary Examiner*—Edward J. Glick
*Assistant Examiner*—Anastasia S. Midkiff
(74) *Attorney, Agent, or Firm*—Weingarten, Schurgin, Gagnebin & Lebovici LLP

(57) ABSTRACT

Apparatus for analysis of a sample includes a radiation source, which is adapted to direct a converging beam of X-rays toward a surface of the sample. At least one detector array is arranged to sense the X-rays scattered from the sample as a function of elevation angle over a range of elevation angles simultaneously, and to generate output signals responsively to the scattered X-rays. The detector array has a first configuration in which the detector array senses the X-rays that are reflected from the surface of the sample at a grazing angle, and a second configuration in which the detector array senses the X-rays that are diffracted from the surface in a vicinity of a Bragg angle of the sample. A signal processor processes the output signals so as to determine a characteristic of the surface layer of the sample.

18 Claims, 5 Drawing Sheets

U.S. PATENT DOCUMENTS

| | | | |
|---|---|---|---|
| 6,507,634 | B1 | 1/2003 | Koppel et al. |
| 6,512,814 | B1 | 1/2003 | Yokhin et al. |
| 6,556,652 | B1 | 4/2003 | Mazor et al. |
| 6,639,968 | B1 | 10/2003 | Yokhin et al. |
| 6,643,354 | B1 | 11/2003 | Koppel et al. |
| 6,680,996 | B1 | 1/2004 | Yokhin et al. |
| 6,711,232 | B1 | 3/2004 | Janik |
| 6,744,950 | B1 | 6/2004 | Aleksoff |
| 6,750,952 | B1 | 6/2004 | Grodnensky et al. |
| 6,771,735 | B1 | 8/2004 | Janik et al. |
| 6,977,986 | B1 * | 12/2005 | Beanland et al. ............ 378/34 |
| 2001/0028699 | A1 | 10/2001 | Iwasaki |
| 2001/0043668 | A1 | 11/2001 | Hayashi et al. |
| 2002/0097837 | A1 | 7/2002 | Fanton et al. |
| 2002/0110218 | A1 | 8/2002 | Koppel et al. |
| 2003/0157559 | A1 | 8/2003 | Omote et al. |
| 2004/0052330 | A1 | 3/2004 | Koppel et al. |
| 2004/0156474 | A1 | 8/2004 | Yokhin et al. |
| 2004/0218717 | A1 | 11/2004 | Koppel et al. |
| 2006/0062351 | A1 * | 3/2006 | Yokhin et al. ............... 378/86 |

OTHER PUBLICATIONS

Powell, et al., X-ray diffraction and reflectivity characterization of SiGe superlattice structures, 1992, Semiconductor Science Technology, vol. 7, pp. 627-631.*

Wiener et al., "Characterization of Titanium Nitride Layers by Grazing-Emission X-Ray Fluorescence Spectrometry", in Applied Surface Science 125 (1998), p. 129.

Hayashi et al., "Refracted X-Rays Propagating Near the Surface under Grazing Incidence Condition", Spectrochimica Acta, Part B 54, 1999, pp. 227-230.

Series 5000 Model XTF5011 X-Ray Tube Information, Oxford Instruments Inc., Scotts Valley, GA, U.S.A., Jun. 1998.

Monolithic Polycapillary Lens Information, X-Ray Optical Systems, Inc., Albany, NY, U.S.A., Dec. 29, 1998. (web site: www.xox.com).

S. Di Fonzo et al., "Non-Destructive Determination of Local Strain with 100-Nanometre Spatial Resolution", Nature, vol. 403, Feb. 10, 2000. (web site: www.nature.com).

Hugues Guerault, "Specular reflectivity and off-specular scattering", Tools for roughness investigation, Dec. 2000.

Jones, et al., "Small angle x-ray scattering for sub-100 nm pattern characterization", Applied Physics Letters 83:19 (2003), pp. 4059-4061.

Hu et al., "Small angle x-ray scattering metrology for sidewall angle and cross section of nanometer scale line gratings", Journal of Applied Physics 96:4 (2004), pp. 1983-1987.

Wu et al., "Small angle neutron scattering measurements of nanoscale lithographic features", Journal of Applied Physics 88:12 (2000), pp. 7298-7303.

Kojima, et al., "Structural characterization of thin films by x-ray reflectivity", Rigaku Journal 16:2 (1999), pp. 31-41.

Stommer, "X-ray scattering from silicon surfaces", in Semiconductor International (May 1, 1998).

Yoneda, "Anomalous surface reflection of X Rays", Physical Review 131, pp. 2010-2013, 1963.

Stommer, et al., "Characterization of semiconductor materials by X-ray scattering", Electrochemical Society Proceedings vol. 99-16, pp. 117-133, 1999.

Bowen, et al., "X-Ray metrology by diffraction and reflectivity", Characterization and Metrology for ULSI Technology, 2000 International Conference (American Institute of Physics, 2001).

Ulyanekov, "Introduction to high resolution X-Ray diffraction", Workshop on X-ray characterization of thin layers (Uckley, May 21-23, 2003).

Ito, "X-ray Scattering Method for Determining Pore-Size Distribution in Low-k Thin Films", Presented at the International Sematech Ultra-Low-k Workshop (San Francisco, CA, Jun. 6-7, 2002).

Naudon, et al., "New apparatus for grazing X-ray reflectometry in the angle-resoived dispresive mode", J. Appl. Cryst. 1989, vol. 22, pp. 46-464.

N. Wu, et al, "Substepping and its Application to HST Imaging", Jul. 27, 2003.

Wormington, Characterization of Pore Size Distribution in Low k Dielectrics Using X-ray Reflectivity, presented at the Sematech Gate Stack Engineering Workshop (Austin, Texas, May 2, 2002).

J. Spear, "Metrology for low-k materials", Silknet Aliance, 2003.

J.R. Levine Parrill, et al, "GISAXS—Glancing Incidence Small Angle X-ray Scattering", Journal de Physique IV 3 (Dec. 1993), pp. 411-417.

Jaklevic, et al., "High Rate X-Ray Fluorescence Analysis by Pulsed Excitation", IEEE Transactions on Nuclear Science NS-19:3 (1972), pp. 392-395.

Jaklevic, et al., "Small X-Ray Tubes for Energy Dispersive Analysis Using Semiconductor Spectrometers", Advances in X-Ray Analysis 15 (1972), pp. 266-275.

Jaklevic, et al., "Energy Dispersive X-Ray Fluorescence Spectrometry Using Pulsed X-Ray Excitation", Advances in X-Ray Analysis 19 (1976).

* cited by examiner

COMBINED X-RAY REFLECTOMETER AND DIFFRACTOMETER

FIELD OF THE INVENTION

The present invention relates generally to analytical instruments, and specifically to instruments and methods for thin film analysis using X-rays.

BACKGROUND OF THE INVENTION

X-ray reflectometry (XRR) is a well-known technique for measuring the thickness, density and surface quality of thin film layers deposited on a substrate. Such reflectometers typically operate by irradiating a sample with a beam of X-rays at grazing incidence, i.e., at a small angle relative to the surface of the sample, in the vicinity of the total external reflection angle of the sample material. Measurement of X-ray intensity reflected from the sample as a function of angle gives a pattern of interference fringes, which is analyzed to determine the properties of the film layers responsible for creating the fringe pattern.

A method for analyzing XRR data to determine film thickness is described, for example, in U.S. Pat. No. 5,740,226, to Komiya et al., whose disclosure is incorporated herein by reference. After measuring X-ray reflectance as a function of angle, an average reflectance curve is fitted to the fringe spectrum. The average curve is based on a formula that expresses attenuation, background and surface roughness of the film. The fitted average reflectance curve is then used in extracting the oscillatory component of the fringe spectrum. This component is Fourier transformed to find the film thickness.

U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. No. 5,923,720, to Barton et al., whose disclosure is incorporated herein by reference, also describes an X-ray spectrometer based on a curved crystal monochromator. The monochromator has the shape of a tapered logarithmic spiral, which is described as achieving a finer focal spot on a sample surface than prior art monochromators. X-rays reflected or diffracted from the sample surface are received by a position-sensitive detector.

U.S. Pat. Nos. 6,512,814 and 6,639,968, to Yokhin et al., whose disclosures are incorporated herein by reference, describe an X-ray reflectometry system that includes a dynamic shutter, which is adjustably positionable to intercept the X-rays incident on the sample. This shutter, along with other features of the system, permits detection of XRR fringe patterns with high dynamic range. These patents also disclose improved methods for analysis of the XRR fringe pattern in order to determine thin film properties, including density, thickness and surface roughness. The high dynamic range enables the system to determine these properties accurately not only for the upper thin film layer, but also for one or more underlying layers on the surface of the sample.

XRR may also be used in situ, within a deposition furnace, to inspect thin film layers in production on a semiconductor wafer, as described, for example, by Hayashi et al., in U.S. Patent Application Publication US 2001/0043668 A1, whose disclosure is incorporated herein by reference. The furnace is provided with X-ray incidence and extraction windows in its side walls. The substrate upon which the thin film has been deposited is irradiated through the incidence window, and the X-rays reflected from the substrate are sensed through the X-ray extraction window.

X-ray diffractometry (XRD) is a well-known technique for studying the crystalline structure of matter. In XRD, a sample is irradiated by a monochromatic X-ray beam, and the locations and intensities of the diffraction peaks are measured. The characteristic scattering angles and the scattered intensity depend on the lattice planes of the sample under study and the atoms that occupy those planes. For a given wavelength $\lambda$ and lattice plane spacing d, diffraction peaks will be observed when the X-ray beam is incident on a lattice plane at angles $\theta$ that satisfy the Bragg condition: $n\lambda = 2d \sin \theta$, wherein n is the scattering order. The angle $\theta$ that satisfies the Bragg condition is known as the Bragg angle. Distortions in the lattice planes due to stress, solid solution, or other effects lead to observable changes in the XRD spectrum.

XRD has been used, inter alia, for measuring characteristics of crystalline layers produced on semiconductor wafers. For example, Bowen et al. describe a method for measuring germanium concentration in a SiGe structure using high-resolution XRD in "X-Ray metrology by Diffraction and Reflectivity," *Characterization and Metrology for ULSI Technology,* 2000 *International Conference* (American Institute of Physics, 2001), which is incorporated herein by reference.

SUMMARY OF THE INVENTION

Embodiments of the present invention provide apparatus and methods for rapid XRR- and XRD-based analysis of a sample. A radiation source directs a converging beam of the X-rays toward a surface of the sample, such as a semiconductor wafer. A detector array senses X-rays scattered from the sample as a function of elevation angle over a range of elevation angles simultaneously. The detector array has XRR and XRD configurations. In the XRR configuration, the radiation source and detector array are positioned so that the array senses X-rays that are reflected from the surface of the sample at grazing angles. In the XRD configuration, the radiation source and detector array are positioned so that the array senses X-rays that are diffracted from the surface in a vicinity of the Bragg angle of the sample. A motion assembly may be provided to shift the radiation source and detector array between the XRR and XRD configurations.

A signal processor receives and processes output signals generated by the detector array in order to determine characteristics of the surface layer or layers of the sample. These characteristics may include, for example, layer thickness, density, composition and surface roughness. The combination of XRR and XRD measurements is particularly useful in giving a complete, accurate picture of the features of crystalline surface layers, such as crystalline thin film layers that are formed in the process of integrated circuit fabrication on semiconductor wafers. The novel system configuration provided by embodiments of the present invention permits both XRR and XRD spectra to be acquired with high throughput and to be cross-checked for accuracy, in a manner that is not possible in XRR systems and XRD systems known in the art.

There is therefore provided, in accordance with an embodiment of the present invention, apparatus for analysis of a sample having a surface layer, the apparatus including:

a radiation source, which is adapted to direct a converging beam of X-rays toward a surface of the sample;

at least one detector array, which is arranged to sense the X-rays scattered from the sample as a function of elevation angle over a range of elevation angles simultaneously, and to generate output signals responsively to the scattered X-rays, the detector array having a first configuration, in which the detector array senses the X-rays that are reflected from the surface of the sample at a grazing angle, and a second configuration, in which the detector array senses the X-rays that are diffracted from the surface in a vicinity of a Bragg angle of the sample; and a signal processor, which is coupled to receive and process the output signals generated in the first and second configurations so as to determine a characteristic of the surface layer of the sample.

In some embodiments, the apparatus includes a motion assembly, which is coupled to move the radiation source and the detector array between the first configuration and the second configuration.

In other embodiments, the radiation source includes first and second radiation sources, which are respectively positioned to direct the X-rays toward the sample in the first and second configurations, and the at least one detector array includes first and second detector arrays, which are respectively positioned to receive the scattered X-rays in the first and second configurations.

Typically, the radiation source includes a curved crystal monochromator.

In a disclosed embodiment, the at least one detector array includes a plurality of detector elements, which are arranged to receive the X-rays scattered from the sample, and the range of elevation angles includes at least 2° of elevation.

In some embodiments, the X-rays that are reflected from the sample in the first configuration are characterized by an oscillatory variation of intensity as a function of the elevation angle, and the processor is adapted to analyze the oscillatory variation in order to determine the characteristic of the surface layer. Typically, the characteristic determined by the signal processor includes at least one of a density, a thickness and a surface roughness of the surface layer.

Additionally or alternatively, the X-rays that are diffracted from the surface in the second configuration are characterized by primary and secondary diffraction peaks, and the processor is adapted to analyze a relation of the peaks in order to determine the characteristic of the surface layer. Typically, the characteristic determined by the signal processor includes a composition of the surface layer.

In a disclosed embodiment, the sample includes a semiconductor wafer, and the signal processor is adapted to analyze the output signals so as to determine a quality of a thin film layer formed on the wafer.

There is also provided, in accordance with an embodiment of the present invention, a cluster tool for producing microelectronic devices, including:

a deposition station, which is adapted to form a thin-film layer on a surface of a semiconductor wafer; and an inspection station, including:
a radiation source, which is adapted to direct a converging beam of X-rays toward a surface of the wafer;
a detector array, which is arranged to sense the X-rays scattered from the wafer as a function of elevation angle over a range of elevation angles simultaneously, and to generate output signals responsively to the scattered X-rays, the detector array having a first configuration, in which the detector array senses the X-rays that are reflected from the surface of the wafer at a grazing angle, and a second configuration, in which the detector array senses the X-rays that are diffracted from the wafer in a vicinity of a Bragg angle of the wafer; and
a signal processor, which is coupled to receive and process the output signals generated in the first and second configurations so as to determine a characteristic of the surface layer of the wafer.

There is additionally provided, in accordance with an embodiment of the present invention, apparatus for producing microelectronic devices, including:

a production chamber, which is adapted to receive a semiconductor wafer;

a deposition device, which is adapted to deposit a thin-film layer on a surface of the semiconductor wafer within the chamber;

a radiation source, which is adapted to direct a converging beam of X-rays toward a surface of the wafer in the chamber;

a detector array, which is arranged to sense the X-rays scattered from the wafer in the chamber as a function of elevation angle over a range of elevation angles simultaneously, and to generate output signals responsively to the scattered X-rays, the detector array having a first configuration, in which the detector array senses the X-rays that are reflected from the surface of the wafer at a grazing angle, and a second configuration, in which the detector array senses the X-rays that are diffracted from the wafer in a vicinity of a Bragg angle of the wafer; and a signal processor, which is coupled to receive and process the output signals generated in the first and second configurations so as to determine a characteristic of the surface layer of the wafer.

There is further provided, in accordance with an embodiment of the present invention, a method for analysis of a sample having a surface layer, the method including:

acquiring an X-ray reflectance (XRR) spectrum of the sample by directing a converging beam of X-rays toward a surface of the sample at a grazing angle, and detecting the X-rays scattered from the sample as a function of elevation angle over a first range of elevation angles simultaneously using at least one detector array;

acquiring an X-ray diffraction (XRD) spectrum of the sample by directing the converging beam of X-rays toward the surface of the sample in a vicinity of a Bragg angle of the sample, and detecting the X-rays scattered from the sample as a function of elevation angle over a second range of elevation angles simultaneously using the at least one detector array; and processing the XRR and XRD spectra so as to determine a characteristic of the surface layer of the sample.

The present invention will be more fully understood from the following detailed description of the embodiments thereof, taken together with the drawings in which:

DETAILED DESCRIPTION OF EMBODIMENTS

Figure 1:
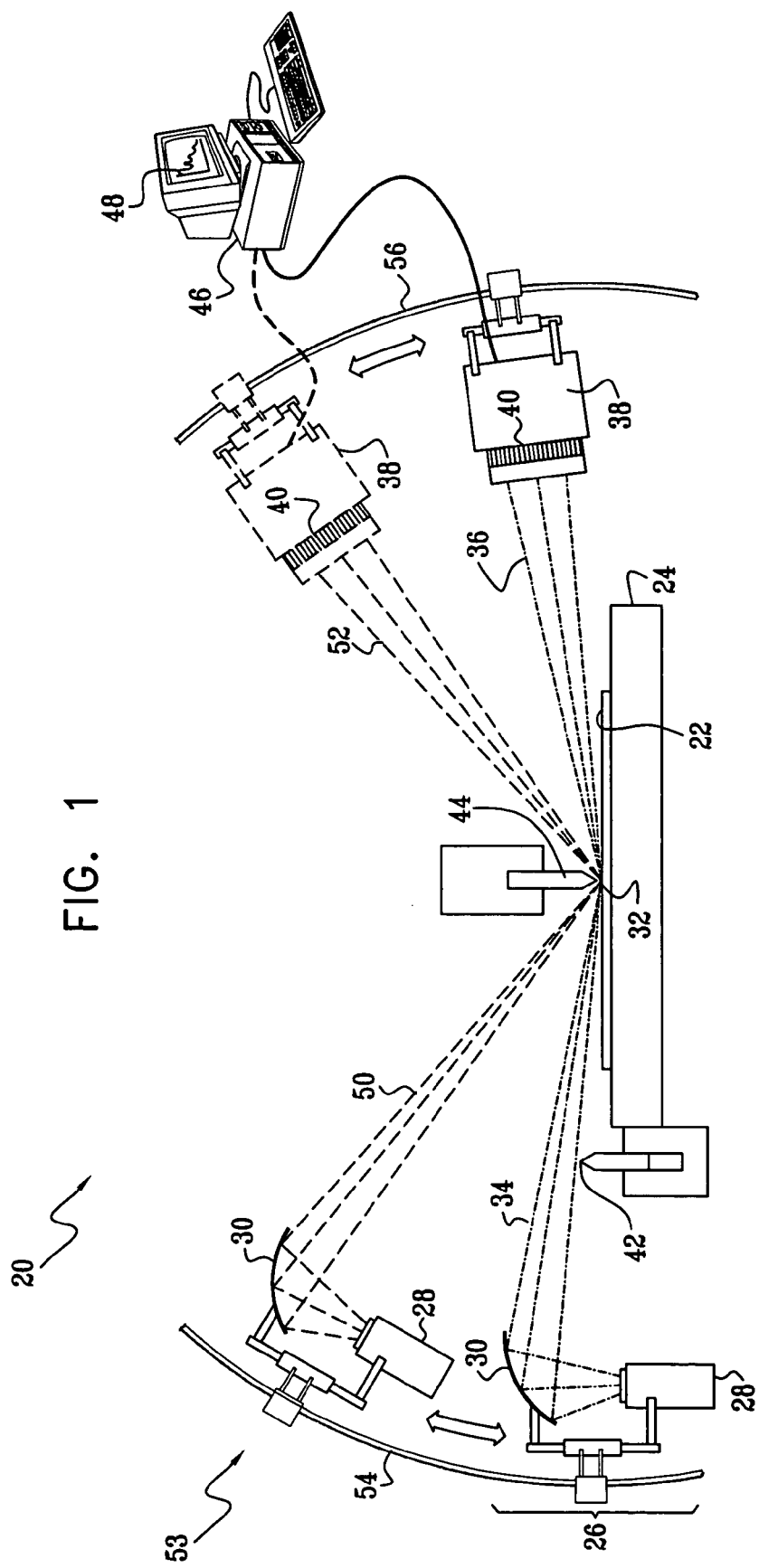
FIG. 1 is a schematic side view of a system for X-ray reflectometry (XRR) and X-ray diffractometry (XRD) measurements, in accordance with an embodiment of the present invention.

Reference is now made to FIG. 1, which is a schematic side view of a system 20 for X-ray reflectometry (XRR) and X-ray diffractometry (XRD) of a sample 22, in accordance with an embodiment of the present invention. Sample 22 is mounted on a motion stage 24, allowing accurate adjustment of the position and orientation of the sample. An X-ray source 26, typically an X-ray tube 28 with monochromatizing optics 30, irradiates a small area 32 on sample 22. X-rays scattered from sample 22 are collected by a detector assembly 38, which comprises a detector array 40, such as a CCD array. Although for simplicity of illustration, only a single row of detectors elements is shown in the figures, with a relatively small number of detector elements, array 40 generally includes a greater number of elements, arranged as either a linear array or a matrix (two-dimensional) array. Further aspects of detector assembly 38 and array 40 are described in the above-mentioned U.S. Pat. No. 6,512,814.

A signal processor 46 receives and analyzes the output of assembly 38, so as to determine a distribution 48 of the flux of X-ray photons reflected from sample 22 as a function of angle at a given energy or over a range of energies. Typically, sample 22 has one or more thin surface layers, such as thin films, at area 32, so that distribution 48 as a function of elevation angle exhibits a structure that is characteristic of interference and/or diffraction effects due to the surface layer and interfaces between the layers. Processor 46 analyzes characteristics of the angular distribution in order to determine characteristics of one or more of the surface layers of the sample, such as the thickness, density, composition and surface quality of the layer, using methods of analysis described hereinbelow.

In the embodiment shown in FIG. 1, X-ray source 26 and detector assembly 38 have two operating configurations: an XRR configuration and an XRD configuration. The XRR configuration is represented in the figure by the drawing of source 26 and detector assembly 38 in solid lines, while the XRD configuration is represented by drawing the source and detector assembly in dashed lines. In the XRR configuration, source 26 irradiates area 32 with a converging beam 34 at a grazing angle, typically over a range of incident angles from about 0° to 4.5°, although larger or smaller ranges may be used. In this configuration, assembly 38 collects a diverging beam 36 of reflected X-rays over a range of angles in the vertical direction, as a function of elevation angle ($\phi$) between about 0° and at least 2°, and typically up to 3°. This range includes angles both below and above the critical angle of the sample for total external reflection, $\Phi_C$. (For clarity of illustration, the angular ranges shown in the figures are exaggerated, as is the elevation of source 26 and detector assembly 38 above the plane of sample 22 in the XRR configuration.)

In the XRD configuration, both source 26 and detector assembly 38 are shifted to higher angles, near the Bragg angle of sample 22. In this configuration, source 26 irradiates area 32 with a converging beam 50 in the vicinity of the Bragg angle, and detector assembly 38 receives a diverging beam 52 over a range of angles in the vicinity of the Bragg angle. For the sake of this example, it is assumed that the lattice plane creating the diffraction pattern is roughly parallel to the surface of sample 22, so that the incidence and takeoff angles defined by beams 50 and 52 relative to the surface are both equal to the Bragg angle. This assumption is often true with respect to semiconductor substrates, such as silicon wafers, and crystalline thin film layers that are grown on such substrates. Alternatively, source 26 and detector assembly 38 may be positioned at different incidence and takeoff angles in order to measure diffraction from lattice planes that are not parallel to the surface of sample 22.

A motion assembly 53 shifts source 26 and detector assembly 38 between the XRR and XRD configurations. In the example shown in FIG. 1, the motion assembly comprises curved tracks 54, 56 along which source 26 and assembly 38 are respectively translated, while maintaining the source and detector assembly at a constant distance from area 32. Other suitable types of motion assemblies for this purpose will be apparent to those skilled in the art.

Alternatively, two separate X-ray sources and/or two separate detector assemblies may be used for the XRR and XRD measurements. In this case, the motion assembly may not be needed. Further alternatively, a single X-ray tube may be shifted between XRR and XRD positions, while each position has its own stationary optics.

Returning now to the components of source 26, tube 28 typically has a small emission area, to permit accurate focusing on the surface of sample 22. For example, tube 28 may comprise the XTF5011 X-ray tube, produced by Oxford Instruments (Scotts Valley, Calif.). A typical X-ray energy for reflectometric and scattering measurements in system 20 is about 8.05 keV (CuKa1). Alternatively, other energies may be used, such as 5.4 keV (CrKa1). A number of different types of monochromatizing optics 30 that may be used in system 20 are described in U.S. Pat. No. 6,381,303, whose disclosure is incorporated herein by reference. For example, the optics may comprise a curved crystal monochromator, such as the Doubly-Bent Focusing Crystal Optic, produced by XOS Inc., of Albany, N.Y. Other suitable optics are described in the above-mentioned U.S. Pat. Nos. 5,619,548 and 5,923,720. The doubly-curved focusing crystal causes beams 34 and 50 to converge in both the horizontal and vertical directions, so as to focus approximately to a point in area 32. Alternatively, a cylindrical optic may be used to focus beams 34 and 50 so that the beam converges to a line on the sample surface. Further possible optical configurations will be apparent to those skilled in the art.

System 20 in the XRR configuration is similar to the XRR system described in the above-mentioned U.S. Pat. No. 6,512,814, with the addition of features and capabilities described herein. In this system, a dynamic knife edge 44 and shutter 42 may be used to limit the angular extent of incident beam 34 of the X-rays in the vertical direction (i.e., perpendicular to the plane of sample 22). Briefly, for optimal detection of low-angle reflections, near 0°, shutter 42 is withdrawn outside the extent of incident beam 34, while knife edge 44 is positioned over area 32 and is lowered to reduce the effective vertical cross-section of the beam. As a result, the lateral dimension of the X-ray spot incident on area 32 is reduced. On the other hand, for effective detection of weaker, high-angle reflections in the XRR configuration, knife edge 44 is withdrawn from beam 34, while shutter 42 is positioned to cut off the low-angle portion of the beam. (Alternatively, the shutter may be positioned to cut off the low-angle portion of reflected beam 36.)

Figure 2:
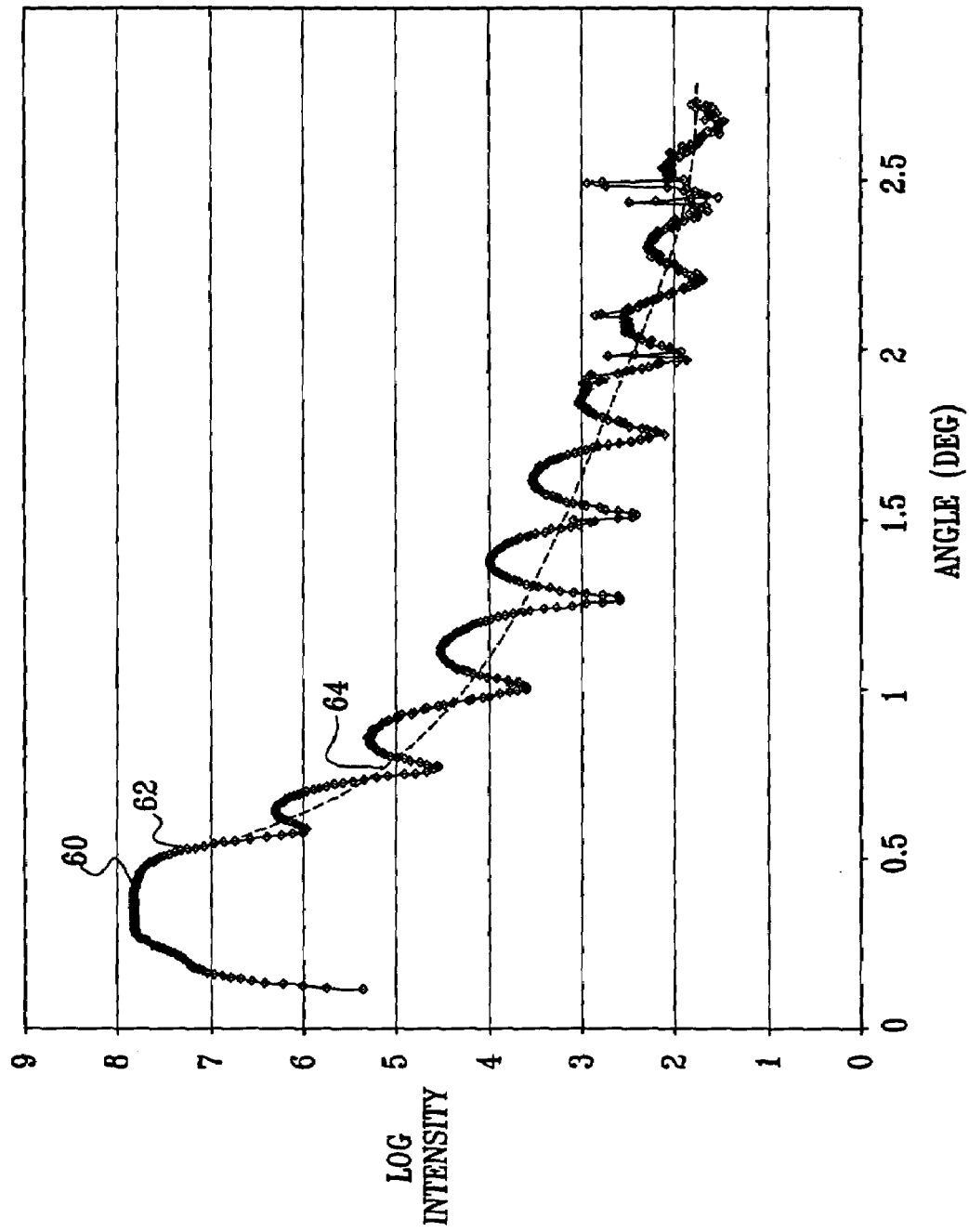
FIG. 2 is a schematic plot of an XRR spectrum, in accordance with an embodiment of the present invention.

FIG. 2 is a schematic plot showing a specular reflection spectrum 60 captured by system 20 in the XRR configuration, in accordance with an embodiment of the present invention. The spectrum is plotted against the elevation angle φ of the reflected X-rays in beam 36. Each data point corresponds to a sum of counts received by a corresponding element, or pixel, of array 40. The signal/noise ratio of the spectrum has been enhanced using techniques described in the above-mentioned U.S. Pat. No. 6,512,814. Spectrum 60 shows a well-defined fringe pattern extending from near 0° out to 2.5°. The spectrum has a characteristic shoulder 62 at the critical angle $\Phi_C$, and drops off in an oscillatory pattern with increasing angle. The location of the shoulder in spectrum 60 may be analyzed to determine the critical angle, and hence the density of the surface layer of sample 22, while the period and amplitude of the oscillations are indicative of the thickness and surface roughness of the surface layer of the sample. The intensity of the higher-order fringes relative to the low-order ones, as indicated by a decay curve 64 fitted to spectrum 60, is determined mainly by the roughness of the outer surface of the sample and, secondarily, of the interfaces between the film layers on the sample.

Figure 3:
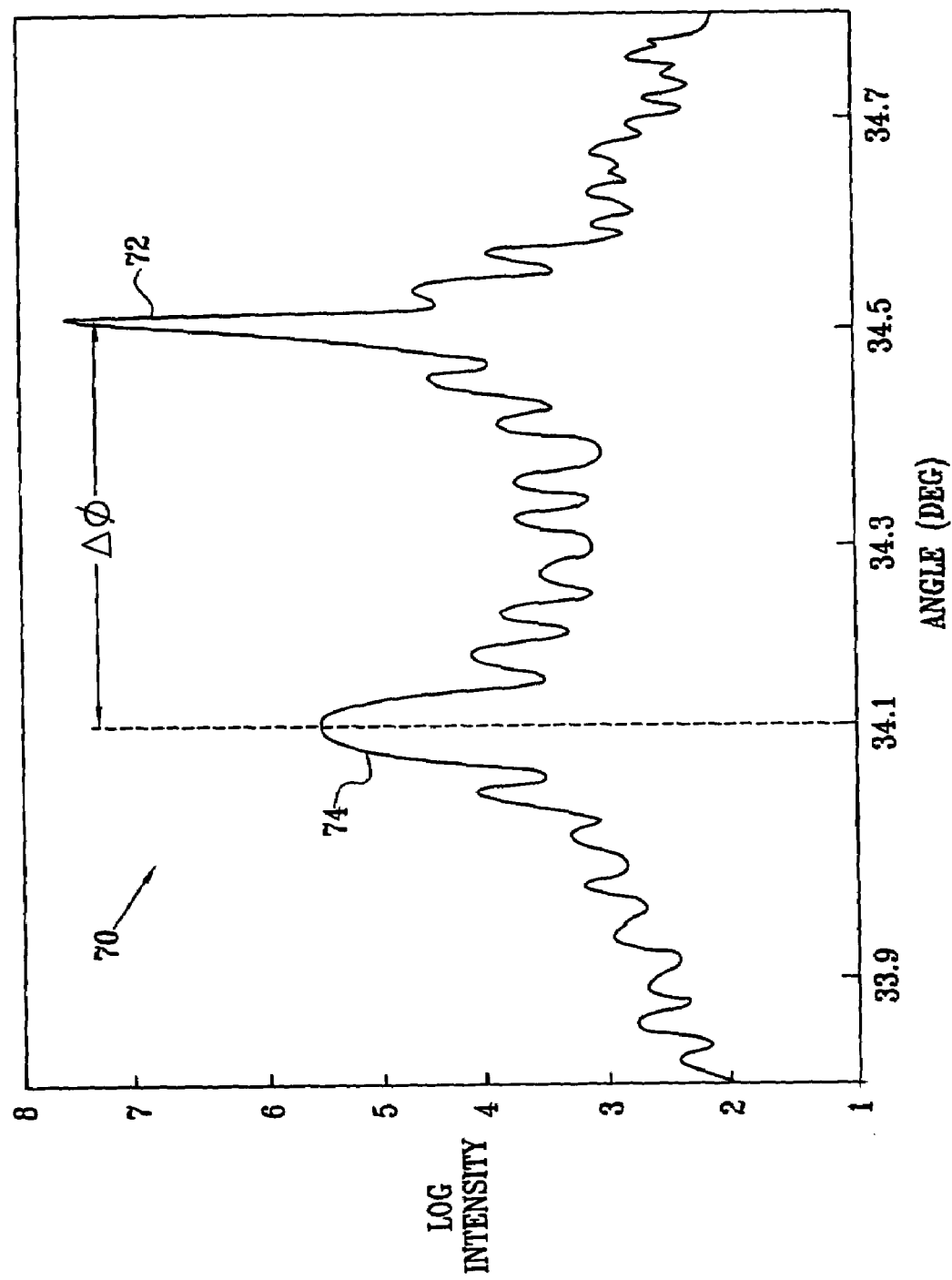
FIG. 3 is a schematic plot of a XRD spectrum, in accordance with an embodiment of the present invention.

FIG. 3 is a schematic plot showing a diffraction spectrum 70 that may be captured by system 20 in the XRD configuration, in accordance with an embodiment of the present invention. The spectrum in this case is plotted against the elevation angle φ of the diffracted X-rays in beam 52. Spectrum 70 is taken from a thin crystalline layer of SiGe, roughly 100 nm thick, which is formed on the surface of a Si wafer. The spectrum comprises a sharp, primary peak 72 at about 34.5°, which is the Bragg angle for Si at 8.05 keV (CuKa1). A secondary peak 74 is also observed, due to deformation of the Si crystal structure by the Ge atoms. The displacement Δφ between peaks 72 and 74 is indicative of the concentration of Ge in the SiGe layer. If spectrum 70 is captured with sufficiently high signal/noise ratio, other features of the spectrum may be resolved and fitted to a mathematic model in order to extract other parameters of the SiGe layer, such as its thickness and the Ge concentration gradient as a function of depth in the layer. Methods that can be used in this sort of analysis are described in the above-mentioned article by Bowen et al. and in a presentation by Ulyanenkov entitled "Introduction to High Resolution X-Ray Diffraction," *Workshop on X-ray Characterization of Thin Layers* (Uckley, May 21–23, 2003), which is incorporated herein by reference.

As noted above, XRR spectrum 60 can also be used to determine the SiGe layer thickness, and the density indicated by the location of shoulder 62 may be used to estimate the Ge concentration. These parameters of the XRR spectrum may be compared with the parameters derived from XRD spectrum 70 in order to verify and improve the precision of the measurements.

As another exemplary application, the XRR and XRD spectra captured by system 20 may be used in analyzing grain size in copper layers that are formed on a semiconductor substrate in the course of integrated circuit fabrication. The grain size characteristics are important because of their impact on electron migration properties.

Figure 4:
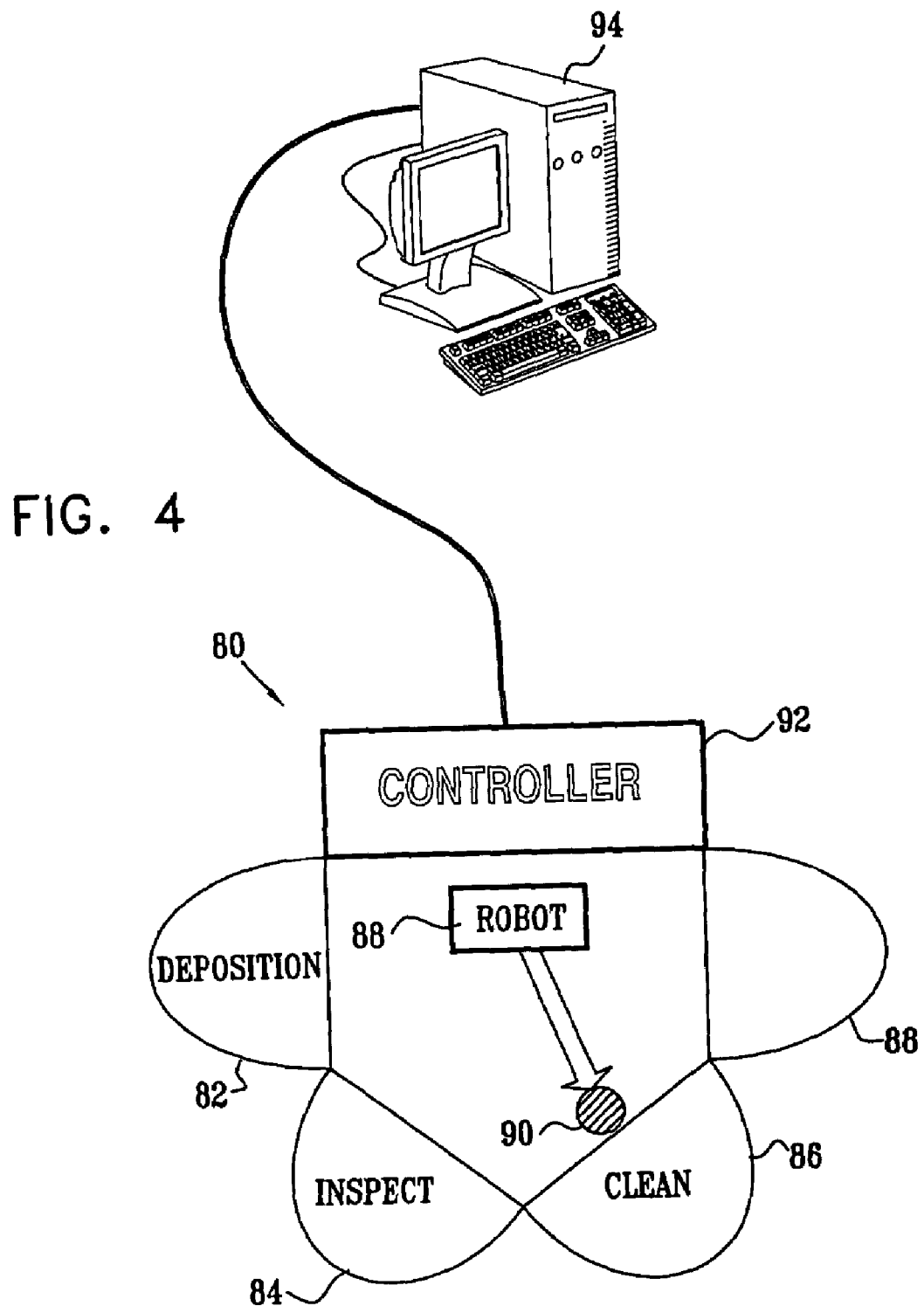
FIG. 4 is a schematic top view of a cluster tool for semiconductor device fabrication, including an inspection station in accordance with an embodiment of the present invention.

FIG. 4 is a schematic top view of a cluster tool 80 for use in semiconductor device fabrication, in accordance with an embodiment of the present invention. The cluster tool comprises multiple stations, including a deposition station 82, for depositing thin films on a semiconductor wafer 90, an inspection station 84, and other stations 86, 88, as are known in the art, such as a cleaning station. Inspection station 84 is constructed and operates in a manner similar to system 20, as described hereinabove. A robot 88 transfers wafer 90 among stations 82, 84, 86, . . . , under the control of a system controller 92. Operation of tool 80 may be controlled and monitored by an operator using a workstation 94, coupled to controller 92.

Inspection station 84 is used to perform X-ray inspection of wafers by XRR and XRD. Such inspection is typically carried out before and/or after selected steps in production processes carried out by deposition station 82 and other stations in tool 80. In an exemplary embodiment, deposition station 82 is used to create thin, crystalline films on wafer 90, and inspection station 84 applies XRR and XRD to evaluate the thickness, density and composition of the films, as described above. Alternatively, at some stages of the process, inspection station 84 may apply one of XRR and XRD, but not the other. Use of station 84 allows early detection of process deviations and convenient adjustment and evaluation of process parameters on production wafers, using controller 92 and possibly workstation 94.

Figure 5:
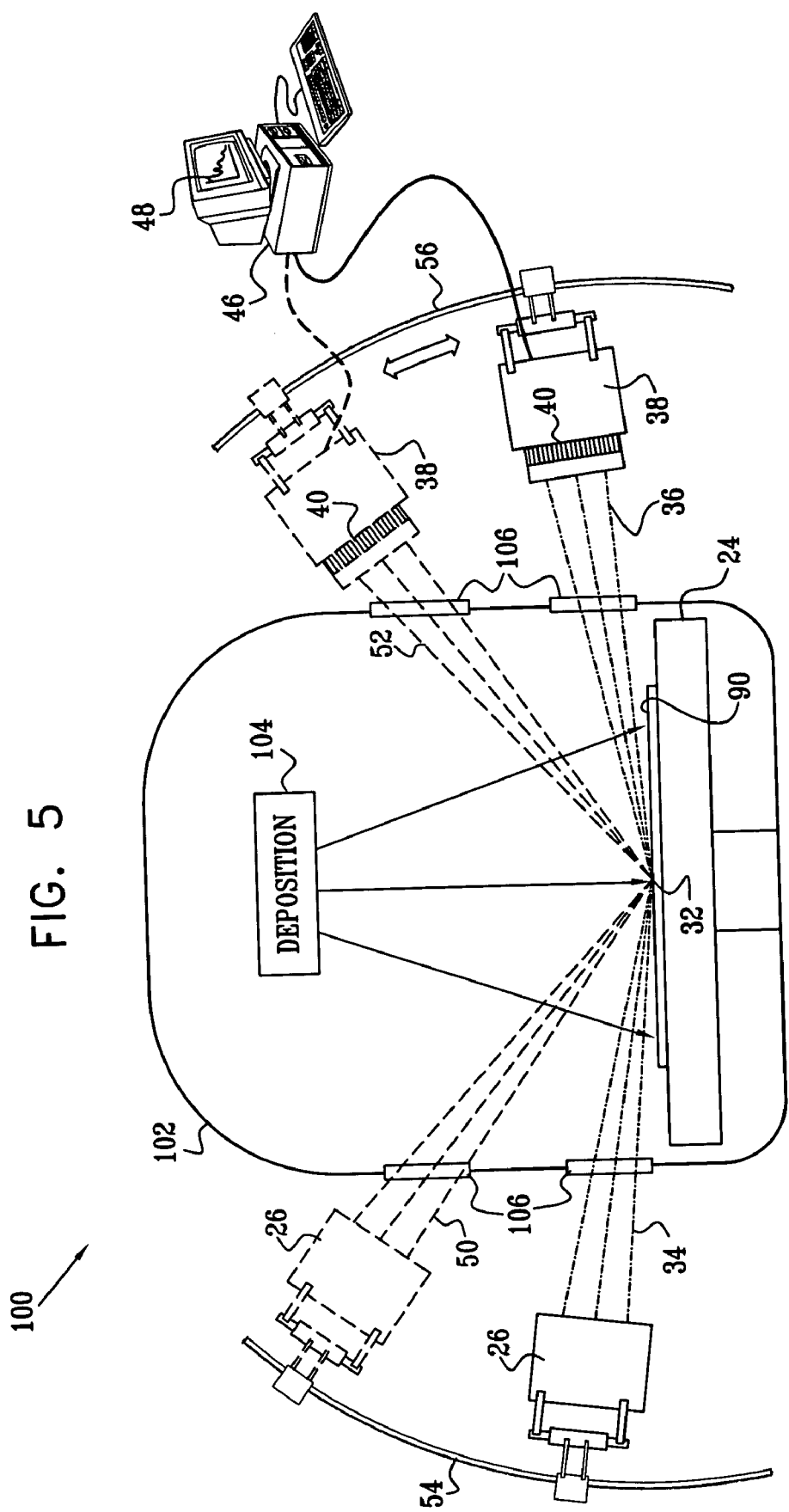
FIG. 5 is a schematic side view of a semiconductor processing chamber with X-ray inspection capability, in accordance with an embodiment of the present invention.

FIG. 5 is a schematic side view of a system 100 for semiconductor wafer fabrication and in situ inspection, in accordance with another embodiment of the present invention. System 100 comprises a vacuum chamber 102, containing deposition apparatus 104, for creating thin films on wafer 90, as is known in the art. The wafer is mounted on motion stage 24 within chamber 102. The chamber typically comprises X-ray windows 106, which may be of the type described in the above-mentioned Patent Application Publication US 2001/0043668 A1. X-ray source 26 irradiates area 32 on wafer 90 via one of windows 106, in either the XRR or the XRD configuration, in the manner described above. Some of the elements shown in FIG. 1 are omitted from FIG. 5 for the sake of simplicity, but typically, elements of this sort are integrated into system 100, as well.

X-rays reflected or diffracted from area 32 are received by array 40 in detector assembly 38 via another one of windows 106. Processor 46 receives signals from detector assembly 38, and processes the signals in order to assess characteristics of thin-film layers in production within chamber 102, by measuring the XRD and/or XRR spectra of wafer 90, as described above. The results of this assessment may be used in controlling deposition apparatus 104 so that the films produced by system 100 have desired characteristics, such as thickness, density, composition and surface roughness.

Although the embodiments described above deal mainly with determining surface layer characteristics of semiconductor wafers, the principles of the present invention can similarly be used in other applications of X-ray-based analysis, as well as in other types of radiation-based analysis, using not only X-rays, but also other ionizing radiation bands. Furthermore, system 20, along with the XRR and XRD techniques described above, may be modified to incorporate other methods of radiation-based analysis, as well. For example, the system may incorporate X-ray fluorescence measurement, as described in the above-mentioned U.S. Pat. No. 6,381,303, and/or small-angle scattering measurements, as described in U.S. patent application Ser. No. 10/364,883, filed Feb. 12, 2003, which is assigned to the assignee of the present patent application and whose disclosure is incorporated herein by reference. Alternatively or additionally, system 20 may be configured to perform diffuse XRR measurements, as described in a U.S. patent application entitled "Enhancement of X-ray reflectometry by measurement of diffuse reflections," filed Jul. 30, 2004, which is likewise assigned to the assignee of the present patent application and whose disclosure is incorporated herein by reference.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for analysis of a sample having a surface layer, the apparatus comprising:
   a radiation source, which is adapted to direct a converging beam of X-rays toward a surface of the sample from a first source location with respect to the sample in which the X-rays impinge on the surface at a grazing angle and from a second source location with respect to the sample at a higher angle than the grazing angle;
   at least one detector array, which is arranged to sense the X-rays scattered from the sample as a function of elevation angle over a range of elevation angles simultaneously, and to generate output signals responsively to the scattered X-rays, the detector array having a first detector location, in which the detector array senses the X-rays that are reflected from the surface of the sample at the grazing angle while the radiation source is in the first source location, and a second detector location, in which the detector array senses the X-rays that are diffracted from the surface in a vicinity of a Bragg angle of the sample while the radiation source is in the second source location;
   a motion assembly, which is coupled to move the radiation source between the first and second source locations and to move the at least one detector array between the first and second detector locations; and
   a signal processor, which is coupled to receive and process the output signals generated by the at least one detector array in the first and second detector locations so as to determine a characteristic of the surface layer of the sample.

2. The apparatus according to claim 1, wherein the radiation source comprises a curved crystal monochromator.

3. The apparatus according to claim 1, wherein the at least one detector array comprises a plurality of detector elements, which are arranged to receive the X-rays scattered from the sample, and wherein the range of elevation angles comprises at least 2° of elevation.

4. The apparatus according to claim 1, wherein the X-rays that are reflected from the sample at the grazing angle are characterized by an oscillatory variation of intensity as a function of the elevation angle, and wherein the processor is adapted to analyze the oscillatory variation in order to determine the characteristic of the surface layer.

5. The apparatus according to claim 4, wherein the characteristic determined by the signal processor comprises at least one of a density, a thickness and a surface roughness of the surface layer.

6. The apparatus according to claim 1, wherein the X-rays that are diffracted from the surface in the vicinity of the Bragg angle are characterized by primary and secondary diffraction peaks, and wherein the processor is adapted to analyze a relation of the peaks in order to determine the characteristic of the surface layer.

7. The apparatus according to claim 6, wherein the characteristic determined by the signal processor comprises a composition of the surface layer.

8. The apparatus according to claim 1, wherein the sample comprises a semiconductor wafer, and wherein the signal processor is adapted to analyze the output signals so as to determine a quality of a thin film layer formed on the wafer.

9. A cluster tool for producing microelectronic devices, comprising:
   a deposition station, which is adapted to form a thin-film layer on a surface of a semiconductor wafer; and
   an inspection station, comprising:
      a radiation source, which is adapted to direct a converging beam of X-rays toward a surface of the wafer from a first source location with respect to the sample in which the X-rays impinge on the surface at a grazing angle and from a second source location with respect to the sample at a higher angle than the grazing angle;
      a detector array, which is arranged to sense the X-rays scattered from the wafer as a function of elevation angle over a range of elevation angles simultaneously, and to generate output signals responsively to the scattered X-rays, the detector array having a first detector location, in which the detector array senses the X-rays that are reflected from the surface of the wafer at the grazing angle while the radiation source is in the first source location, and a second detector location, in which the detector array senses the X-rays that are diffracted from the wafer in a vicinity of a Bragg angle of the wafer while the radiation source is in the second source location;
      a motion assembly, which is coupled to move the radiation source between the first and second source locations and to move the at least one detector array between the first and second detector locations; and
      a signal processor, which is coupled to receive and process the output signals generated by the at least one detector array in the first and second detector locations so as to determine a characteristic of the surface layer of the wafer.

10. Apparatus for producing microelectronic devices, comprising:
   a production chamber, which is adapted to receive a semiconductor wafer;
   a deposition device, which is adapted to deposit a thin-film layer on a surface of the semiconductor wafer within the chamber;
   a radiation source, which is adapted to direct a converging beam of X-rays toward a surface of the wafer in the chamber from a first source location with respect to the sample in which the X-rays impinge on the surface at a grazing angle and from a second source location with respect to the sample at a higher angle than the grazing angle;
   a detector array, which is arranged to sense the X-rays scattered from the wafer in the chamber as a function of elevation angle over a range of elevation angles simultaneously, and to generate output signals responsively to the scattered X-rays, the detector array having a first detector location, in which the detector array senses the X-rays that are reflected from the surface of the wafer at the grazing angle while the radiation source is in the first source location, and a second detector location, in which the detector array senses the X-rays that are diffracted from the wafer in a vicinity of a Bragg angle of the wafer while the radiation source is in the second source location;

a motion assembly, which is coupled to move the radiation source between the first and second source locations and to move the at least one detector array between the first and second detector locations; and a signal processor, which is coupled to receive and process the output signals generated by the at least one detector array in the first and second detector locations so as to determine a characteristic of the surface layer of the wafer.

11. A method for analysis of a sample having a surface layer, the method comprising:

acquiring an X-ray reflectance (XRR) spectrum of the sample by directing a converging beam of X-rays from a radiation source at a first source location with respect to the sample toward a surface of the sample at a grazing angle, and detecting the X-rays scattered from the sample as a function of elevation angle over a first range of elevation angles simultaneously using at least one detector array in a first detector location;

acquiring an X-ray diffraction (XRD) spectrum of the sample by directing the converging beam of X-rays from the radiation source at a second source location with respect to the sample toward the surface of the sample at a higher angle than the grazing angle, and detecting the X-rays scattered from the sample as a function of elevation angle over a second range of elevation angles in a vicinity of a Bragg angle of the sample simultaneously using the at least one detector array in a second detector location;

moving the radiation source between the first and second source locations, and moving the at least one detector array between the first and second detector locations; and processing the XRR and XRD spectra so as to determine a characteristic of the surface layer of the sample.

12. The method according to claim 11, wherein directing the converging beam comprises focusing the X-rays using a curved crystal monochromator.

13. The method according to claim 11, wherein the at least one detector array comprises a plurality of detector elements, which are arranged to receive the X-rays scattered from the sample, and wherein the range of elevation angles comprises at least 2° of elevation.

14. The method according to claim 11, wherein the XRR spectrum is characterized by an oscillatory variation of intensity as a function of the elevation angle, and wherein processing the spectra comprises analyzing the oscillatory variation in order to determine the characteristic of the surface layer.

15. The method according to claim 14, wherein the characteristic of the surface layer comprises at least one of a density, a thickness and a surface roughness of the surface layer.

16. The method according to claim 11, wherein the XRD spectrum is characterized by primary and secondary diffraction peaks, and processing the spectra comprises analyzing a relation of the peaks in order to determine the characteristic of the surface layer.

17. The method according to claim 16, wherein the characteristic of the surface layer comprises a composition of the surface layer.

18. The method according to claim 11, wherein the sample comprises a semiconductor wafer, and wherein processing the spectra comprises analyzing the output signals so as to determine a quality of a thin film layer formed on the wafer.

* * * * *